United States Patent

Volz-Thomas et al.

[11] Patent Number: 5,153,139
[45] Date of Patent: Oct. 6, 1992

[54] METHOD AND APPARATUS FOR MEASURING THE WATER SOLUBLE STRONG ACIDS SUSPENDED IN AIR

[75] Inventors: Andreas Volz-Thomas, Erkelenz-Hetzerath; Andreas Vetter, Mönchengladbach; Stefan Gilge, Stolberg; Dieter Kley, Julich, all of Fed. Rep. of Germany

[73] Assignee: Forschungszentrum Jülich GmbH, Julich, Fed. Rep. of Germany

[21] Appl. No.: 664,947

[22] Filed: Mar. 5, 1991

[30] Foreign Application Priority Data

Mar. 5, 1990 [DE] Fed. Rep. of Germany ....... 4006852

[51] Int. Cl.$^5$ ............................................. G01N 33/24
[52] U.S. Cl. ........................................ 436/32; 436/100; 436/33; 436/175; 436/178; 73/31.01; 73/31.07
[58] Field of Search ................... 436/32, 33, 100, 102, 436/101, 150, 151, 163, 175, 178; 73/31.01, 31.07, 19.12; 55/19

[56] References Cited

U.S. PATENT DOCUMENTS

| | | |
|---|---|---|
| 3,114,610 | 12/1963 | Gafford et al. ................. 436/163 |
| 3,546,079 | 12/1970 | Waclawik et al. ............... 436/101 |
| 3,725,009 | 4/1973 | Lovelock ........................... 435/175 |
| 3,926,560 | 12/1975 | Gentry .............................. 436/101 |
| 4,272,479 | 6/1981 | Huneke et al. ................... 436/100 |
| 4,304,752 | 12/1981 | Jenkins et al. ................... 436/175 |
| 4,792,526 | 12/1988 | Ouellette et al. ................ 436/175 |

Primary Examiner—James C. Housel
Assistant Examiner—Lien Tran
Attorney, Agent, or Firm—Frishauf, Holtz, Goodman & Woodward

[57] ABSTRACT

Measurements of acids in air can be greatly falsified by the content of carbon dioxide in the air in spite of the low solubility of carbon dioxide in water and its low dissociation constant. When the measurements are made after a simple absorption of the acid residues in the air in an absorption solution. The air separated from the absorption solution on its way to measurement is cleaned of carbon dioxide by exposure to silica gel and sodalime and then is used to clean the absorption solution of carbon dioxide in a similar exposure of air to the liquid. The measurement of the acidity of the solution thus cleaned of carbon dioxide provides reliable measurements of strong acid residues in air and can be carried out on a continuous basis.

7 Claims, 1 Drawing Sheet

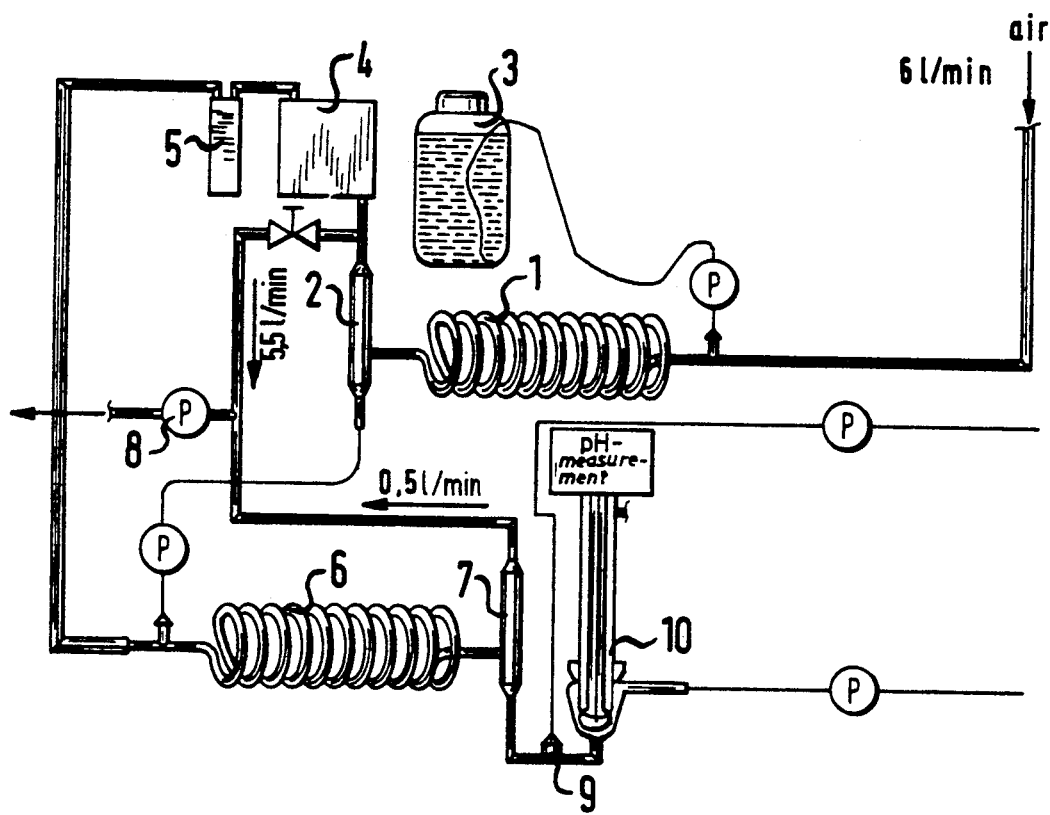

5,153,139

METHOD AND APPARATUS FOR MEASURING THE WATER SOLUBLE STRONG ACIDS SUSPENDED IN AIR

Cross-Reference to Related Copending Application the Disclosure of Which is hereby Incorporated by Reference Ser. No. 07/581,276, filed Sep. 12, 1990, Application of Dieter Kley, Stefan Gilge, Jelena Jeftic and Andreas Volz-Thomas.

BACKGROUND OF THE INVENTION

1. Field of the Invention

This invention concerns a method for determining the content of water soluble strong acids in air in which the air is passed in contact with a watery liquid and then again separated from the liquid. The invention further concerns an apparatus for determining the content of water soluble strong acids in air, in which in a first stage air is passed in contact with a watery liquid and the strong acids are dissolved therein.

2. Description of Related Art

The analysis of trace elements in the atmosphere is becoming more important with the air pollution that is always becoming more problematic. The strong acids, for example nitric acid, sulfuric acid and hydrochloric acid, which are either admitted directly into the air or arise in the air as products of pollution emissions, play a particularly strong role in the problems of cleaning the air. Because of their high solubility in water, the acids dissolve in precipitation and because of their great dissociation constants ($K_s > 1$ mol/l) they dissociate completely into the corresponding anions and $H_3O^+$. Finally they reach the ground with the precipitation ("acid rain"). Measurements and investigations for determining the concentration of the water soluble strong acids in the air are of importance for estimating the acidity that appears in precipitation and, particularly, the determination of this concentration of strong acids in air leads to conclusions concerning the transformation of air pollution and also makes possible the development of strategy for reducing the acid content of rain. It is not so much the identification of particular acids that is of importance, but rather the determination of the aggregate content of as $H_3O^+$ ions present in a volume of air and capable of being set loose when taken up in water. These magnitudes can be designated as potential acidity.

In order to determine trace elements and monitor them, it is not only important that the measuring process should be sufficiently accurate. The measuring process should also be economic to install, for example, in measuring vehicles, should be simple and should be capable of being carried out with simple equipment. This applies in the present case, since investigations need to be carried out also in upper regions of the atmosphere, where it is desirable for the measurement apparatus to be installed in a balloon sonde.

The presently known measurement processes for determining acids in air are concerned with the determination of the individual components and involves a high cost in instrumentation and operative timing. They are capable of being installed only on the ground or at best in airplanes and in large dirigibles or balloons. The known simple measurement processes for determining acidity are usable only in a discontinuous manner for analysis of precipitation that has already fallen.

SUMMARY OF THE INVENTION

It is an object of the present invention to provide a measuring process of the kind above-described, as well as the apparatus therefor, which is simple and nevertheless sufficiently sensitive and accurate and permits its use in economical apparatus.

The air quantity to measured is passed over an absorption solution, such as water, and is carried along with it, and thereafter again separated from it. The solution then contains the acids in question and also carbon dioxide which is a disturbing material. In accordance with the invention the solution is submitted to a second method step in which air which has been cleaned of any carbon dioxide is brought into contact with the solution so that the solution is essentially cleaned of carbon dioxide without removing the dissolved strong acids. The solution containing the strong acids is then made to flow through a measuring cell with a combined pH-electrode with a measuring indicator connected to it in which the acidity of the solution is determined continuously and then, taking account of the amount of air to be analyzed and the quantity of absorption solution that has passed, the concentration of strong acids in air determined and indicated.

The air that is used for removing the carbon dioxide can be the same air which is separated from the solution after the first stage of analysis, being first put through a packing of silica gel and soda-lime for freeing it from carbon dioxide, and then humidified by passing through a washing stage before using the air to remove the carbon dioxide from the solution.

BRIEF DESCRIPTION OF THE DRAWING

The apparatus aspect of the invention, as well as some aspects of the method will be better understood in the detailed description that follows with reference to the annexed drawing, the single FIGURE of which is an apparatus for the practice of the invention shown in diagrammatic form.

DESCRIPTION OF THE PREFERRED EMBODIMENT

The first stage of the apparatus consists of a collecting coil or absorption spiral 1 which leads to a gas separator 2 and is also connected to a supply holding vessel 3. Air to be analyzed passes into the gathering (absorption) spiral 1 where it travels together with the aqueous absorption liquid which is supplied out of the vessel 3. The air comes into contact intimately with the liquid as the air passes through the spiral. In this absorption the strong acids to be analyzed are completely dissolved, but an equilibrium is established for the $CO_2$. The absorption solution and the air are then separated from each other in the gas separator 2.

At this point the process aspect of the first stage should be examined more closely. Although the air to be analyzed is first brought along in a known way over or with a liquid layer which for example can be provided by a collecting spiral, the collecting stage is so dimensioned in this case that the acids to be analyzed are practically completely (99%) taken up into the liquid.

The air and the solution are then separated.

In the aqueous solution the strong acids dissociate in accordance with the action (1) below, completely into their anions and $H_3O^+$ cations.

$$H_nA + nH_2O \rightarrow A^{n-} + nH_3O^+ \quad (1)$$

The symbol n in the above reaction equation designates the value (quantity unit of solution) of the acids present. The concentration of the cations $H_3O^+$ that then sets in is generally designated as the acidity of the solution and can be determined in a simple way, for example by means of an electrochemical process that is carried out in a commercially available pH measuring cell. As for the carbon dioxide, the considerations are as follows. Carbon dioxide is present in substantially large concentrations in the air. The carbon dioxide in the air that is measured is partly dissolved in the liquid. Carbon dioxide is a weak acid and reacts with water to form $HCO_3^-$ and $H_3O^+$. This interferes with the analysis of the strong acids and can make the results totally useless. At a typical concentration of strong acids of 1 ppb (corresponding to $10^{-9}$ mol acid/mol air) in the air, and with a suction power of 6 liters per minute and a flow of the water solution of $10^{-3}$ l/min, an almost 100% collection efficiency can be obtained in solution, resulting in a solution acidity as follows:

$$(6 \ l/min / 22.4 \ l/mol) \times 10^{-9} \ mol/mol \times 10^3 \ min/l = 2.7 \times 10^{-7} \ mol/l \quad (2)$$

In contrast therewith, because of the universal presence in the atmosphere of higher concentrations of 350,000 ppb of $CO_2$, in spite of the slight solubility of $CO_2$ (its Henry constant, is $3.1 \times 10^{-2}$ mol/l bar) and its essentially slight dissociation constant compared to those of the strong acids ($K_{s1} = 4.3 \times 10^{-7}$ mol/l), an acidity about 10 times higher is obtained:

$$(3.5 \times 10^{-4} \ bar \times 3.1 \times 10^{-2} \ mol/l \ bar \times 4.3 \times 10^{-7} \ mol/l)^{0.5} = 2.2 \times 10^{-6} \ mol/l \quad (3)$$

In that way the analysis for the strong acids is falsified in a strongly non-negligible manner. That explains the necessity of the second stage of the process and apparatus of the invention.

The apparatus of the second stage comprises gas cleaning units 4 and 5, a desorption spiral 6 and a second gas separator 7. The air separated by the gas separator 2 goes to the gas cleaning units, the first containing a bed 4 of silica gel and soda-lime (for removal of residual $CO_2$) and a following washing vessel 5 (for remoistening the air). The cleaned air goes into the desorption spiral 6 where it is carried along with the absorption solution which is supplied from the gas separator 2. The air is thereafter separated from the solution in a second gas separator 7 and drawn off by the pump 8.

Since it is not necessary to clean all the air from gas separator 2 to have enough clean air for the desorption spiral 6, a valve 11 is provided by which the pump 8 can be used to exhaust the gas from the separator 2 that does not need to go to through the units 4 and 5 to the spiral 6. As shown in the drawing, in the illustrated case only 0.5 liter/min. out of a total flow of 6 liters/min. needs to be fur utilized.

The pumps designated P are shown in other parts of the apparatus. They serve the necessity of keeping the flows going in the proper directions and at the right velocities, which should be consistent with the desired flow rate of input air and absorption solution input. These are peristaltic pumps for which the throughput rate can be optimized by selection of the rate of revolution of the mechanism and the tube diameter:

The special value of the invention lies in the removal of the disturbing $CO_2$ from the solution. It depends upon the providing of a carbon dioxide free gas for flushing out the carbon dioxide from the absorption solution and this can of course be from any particular source rather in than the manner shown in the drawing. In the desorption spiral 6 the $HCO_3^-$ and $CO_2$ present in the solution are practically entirely (about 99%) removed from the solution and, on the other hand, the concentration of the strong acids to be analyzed is practically uneffected (by less than 1%). The system shown in the drawing is particularly economical because the air to be analyzed is itself used as the source of gas free of carbon dioxide, since the cleaning of the carbon dioxide from this gas after the strong acids have been removed is no more expensive than cleaning any other air of carbon dioxide for the use in this process. In the unit 4 containing the silica gel and the soda-lime the $CO_2$ present in the air is converted into a carbonate which is non-volatile.

By the optimal dimensioning of the desorption spiral and of the rate of gas flow it is possible to obtain the result that the residual acidity ascribable to the $CO_2$ in the solution is less than $3 \times 10^{-8}$ mol/l, i.e. only about 10% of the originally measured value (equation (3)). Since the atmospheric $CO_2$ concentration fluctuates by about 20% in both directions, the acidity contributed by the $CO_2$ now provides an uncertainty of the measurement value of about 2%.

The first stage puts the acids into solution, the second removes of the carbon dioxide and now the third stage provides the determination of the acidity.

Before entering the measuring stage the solution passes into the gas separator 7 and thereafter passes through a bubble remover before going into a measuring device 10. This is a pH measuring device in which the $H_3O^+$ concentration is continuously determined.

In the present case a particularly well-suited pH meter is used which is commercially available and has a measurement cell of small volume (0.5 ml) which is optimal for operation with flowing media. It is known as a combined pH-electrode for the determination of small amounts of solute in flowing liquids Manufacturer: Ingold Messtechnik GmbH).

In order to reduce the signal noise of the pH electrode, there is added to the water solution in the supply vessel 3 a conductive salt (for example potassium chloride in a concentration of 0.5 mol per liter).

As already mentioned it is to be taken into account that gas bubbles carried along in the liquid disturb the pH measurement. This is the reason for the provision of the bubble separator 9.

Since the concentration of the strong acids is calculated from the meausred acidity, the quantity of air drawn into the system in each unit of time and the flow of absorption solution, those rates of flow being essentially proportionality factors, it is necessary for highly accurate methods to provide a measurement or regulation of the flows in well known ways. The overall sensitivity of the measuring apparatus can be determined in conventional ways, for example by use of a calibrated acid source (permeation tube).

EXAMPLE OF PROCESS OPERATION

With the above-described apparatus the process can be carried out as described in the following example.

(a) Collection Stage

With a total concentration of strong acids of 1 ppb in air to be measured (defined as moles of acid times value per mole of air), a suction power of 6 l per minute and an absorption solution flow of $10^{-3}$ l/min, there is obtained a $H_3O^+$ concentration in the absorption solution of $$(6\ l/min/22.4\ l/mol) \times 10^{-9}\ mol/mol \times 10^3 \quad min/l = 2.7 \times 10^{-7}\ mol/l \tag{4}$$

Apart from the above absorption, at atmospheric pressure of 1 bar, as the result of the presence of 350,000 ppb of $CO_2$ in the air there is produced a concentration of $H_3O^+$ given by equation (5) below. This equation takes account of the solubility and dissociation equilibria: $CO_2$ solubility of $3.1 \times 10^{-2}$ mol/l·bar and dissociation constant $K_{s1} = 4.3 \times 10^{-7}$ mol/l.

$$(3.5 \times 10^{-4}\ bar\ mol/mol \times 3.1 \times 10^{-2}\ mol/l \quad bar \times 4.3 \times 10^{-7}\ mol/l)^{0.5} 2.2 \times 10^{-6}\ mol/l \tag{5}$$

The concentration of dissolved $HCO_3^-$ is likewise about $2.2 \times 10^{-6}$ mol/l (the further dissociation into $CO_3^{2-}$ is negligible under these conditions—$K_{2s} = 5.6 \times 10^{-11}$). The concentration of dissolved $CO_2$ is $$3.5 \times 10^{-4}\ bar\ mol/mol \times 3.1 \times 10^{-2}\ mol/l \quad bar = 1.1 \times 10^{-5}\ mol/l \tag{6}$$

At the end of the collection stage, the gaseous and liquid phases are separated.

(b) Removal of $CO_2$

In the cleaning of the gas a portion of the air (0.5 l/min.) is passed over a bed of silica gel and soda-lime 4 (100 g of each suffice for 10 hours of operation) and is thereby dried and completely freed of $CO_2$. The $CO_2$-free air is then remoistened in the washing vessel 5 and then supplied to the desorption spiral 6 to which the absorption solution is also supplied from the gas separator 2. A predominant portion of the $CO_2$ then goes into the gas phase and the residual acidity in the solution caused by $CO_2$ is then as follows:

$$(1.3 \times 10^{-5}\ mol/l \times 10^{-3}\ l/min \times 22.4 \quad l/mol \times 3.1 \times 10^{-2}\ l/mol/bar \times 4.3 \times 10^{-7} \quad mol/l)/(3 \times 10^{-7}\ mol/l \times 0.5\ l/min) = 2.6 \times 10^{-8} \quad mol/l \tag{7}$$

Because of the natural fluctuations of atmospheric $CO_2$ concentration, the above value for the acidity caused by $CO_2$ has an uncertainty, in both directions, of 10%.

(c) Determination of Acidity

When the $H_3O^+$ concentration is continuously determined in the measuring cell 10 and its associated equipment, over 90% of the measured values result from the presence of strong acids.

The illustrative values given above, where all these factors come in, give a good example of the relative magnitude of flows that is desirable in the operation of the apparatus of the invention and in the use of the process generally.

Although the invention has been described with reference to a particular illustrated embodiment of apparatus, it will be recognized that variations and modifications are possible within the inventive concept. For example, $CO_2$ can be removed from air by bubbling through an alkaline solution, but so doing would have the disadvantage of making the apparatus more bulky and more troublesome to service.

We claim:

1. A process for measuring the atmospheric content of soluble acids comprising the steps of:

passing atmospheric air, at a measured rate of air flow, though a path enclosed so as to exclude unmeasured air, said path including a first absorption portion (1) in which there flows an aqueous absorption solution in contact with said measured-rate air passing therethrough;

using a first separating device (2) in said path to separate the air exiting from said first absorption portion (1) of said path from said aqueous absorption solution exiting therefrom;

passing the aqueous absorption solution exiting from said first separating device (2) through a second absorption portion (6) in said path in which air free of carbon dioxide flows in contact with said aqueous absorption solution exiting from said first separating device;

using a second separating device (7) in said path to separate the air exiting from said second absorption portion (6) in said path from said aqueous absorption solution exiting therefrom, and passing said aqueous absorption solution exiting from said second separating device (7) in said path through a measuring cell having, a pH measuring electrode and an indicator of the acidity of said atmospheric air with reference to relative magnitudes of rate of flow of said solution and of said measured rate of air flow.

2. The process of claim 1, further comprising the following steps;

removing the carbon dioxide content of said air exiting from said first separating device (2) of said path by passing said exiting separated air through a container (4) containing aggregate of dry alkali material, thereafter passing air exiting from said container through a wash chamber for remoistening, thereby producing remoistened clean air, and supplying said remoistened clean air, previously cleaned and freed of carbon dioxide, to said second absorption portion (6) in said path (6).

3. The process of claim 2, in which said aggregate of dry alkali material is an aggregate of silica gel and soda-lime.

4. The process of claim 1, wherein the flow of said aqueous absorption solution through said first (1) and second (6) absorption portions of said path is in the same direction as the flow of air therethrough.

5. The process of claim 2, wherein the flow of said aqueous absorption solution through said first (1) and second (6) absorption portions of said path is in the same direction as the flow of air therethrough.

6. The process of claim 1, wherein said aqueous absorption solution exiting from said second separating device is subjected to removal of bubbles therefrom (9) before entering said measuring cell.

7. The process of claim 2, wherein said aqueous absorption solution exiting from said second separating device is subjected to removal of bubbles therefrom (9) before entering said measuring cell.

* * * * *

UNITED STATES PATENT AND TRADEMARK OFFICE
CERTIFICATE OF CORRECTION

PATENT NO. : 5,153,139
DATED : October 6, 1992
INVENTOR(S) : Volz-Thomas et al.

It is certified that error appears in the above-indentified patent and that said Letters Patent is hereby corrected as shown below:

On the title page: Item [54] and Column 1, line 3, delete, "STRONG"

Column 6, line 11 (claim 1), change "though" to --through--

Column 6, line 48 (claim 2), change "path (6)" to --path,--

Signed and Sealed this

Ninth Day of July, 1996

Attest:

BRUCE LEHMAN

Attesting Officer          Commissioner of Patents and Trademarks